Figure 1:
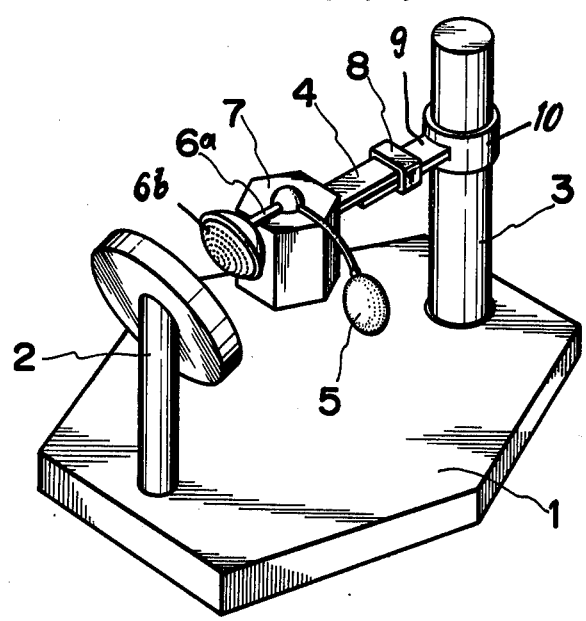

United States Patent [19]

Masuda et al.

[11] 4,146,433
[45] Mar. 27, 1979

[54] METHOD AND APPARATUS FOR ASSESSING ANTI-BACTERIAL ACTIVITY OF ANTIBIOTICS

[75] Inventors: Gohta Masuda, 15-48 Gamou, Kotobuki-cho, Koshigaya-shi, Saitama-ken, Japan; Susumu Tomioka, Tokyo, Japan

[73] Assignee: Gohta Masuda, Saitama, Japan

[21] Appl. No.: 855,612

[22] Filed: Nov. 29, 1977

[30] Foreign Application Priority Data

Nov. 30, 1976 [JP] Japan .............................. 51/142928

[51] Int. Cl.² .............................................. C12K 1/04
[52] U.S. Cl. ............................... 195/103.5 K; 195/127
[58] Field of Search ................ 195/103.5 K, 103.5 M, 195/127, 139

[56] References Cited

U.S. PATENT DOCUMENTS

| | | | |
|---|---|---|---|
| 3,451,893 | 6/1969 | Sanders | 195/103.5 M |
| 3,772,154 | 11/1973 | Isenberg et al. | 195/127 X |
| 3,776,817 | 12/1973 | Van Der Pfoedten | 195/103.5 K |

Primary Examiner—Raymond N. Jones
Assistant Examiner—Robert J. Warden
Attorney, Agent, or Firm—Michael J. Striker

[57] ABSTRACT

A novel and time saving method for assessing bactericidal activities of antibiotics on agar plates is described. Minimal inhibiting concentrations (MIC) are determined by the agar dilution method. An antibiotic inactivating enzyme solution is sprayed onto the plates to inactivate the antibiotic. After further incubation, the minimal concentration at which no visible growth occurred on the plates is determined and is defined as minimal bactericidal concentration (MBC).

10 Claims, 2 Drawing Figures

METHOD AND APPARATUS FOR ASSESSING ANTI-BACTERIAL ACTIVITY OF ANTIBIOTICS

This invention relates to a novel method for assessing bacteriostatic and bactericidal activities of antibiotics on agar plates. More particularly, this invention relates to a method for assessing bacteriostatic and bactericidal activities of β-lactam antibiotics on agar plates. Still more particularly, this invention relates to a method for assessing bacteriostatic and bactericidal activities of β-lactam antibiotics with respect to a number of bacterial strains and also relates to a novel devices for facilitating the carrying out of such method.

In general, minimal bactericidal concentrations are higher than minimal bacteriostatic or inhibitory concentrations for a given antibiotic. The aforesaid concentrations reflect the degree of antibacterial activity of the antibiotic. Heretofore, the methods conventionally employed for making these determinations have been the loop transfer following the broth dilution method.

The broth dilution method is both expensive and time consuming since it requires large numbers of test tubes, pipettes, as well as other instrumentation, the procedure involved being both complicated and troublesome. Further, only a limited number of bacteria and antibiotics can be studied with this method.

However, the broth method has been considered indispensable in spite of the complicated and time-consuming techniques involved in its use as it provides the only method whereby the bactericidal concentrations of antibiotics can be assessed by examining the presence or absence of surviving bacteria following transfer of the broth to the agar plates. While the agar plate method is, by comparison, relatively simple and can be used with a large number of test strains and antibiotics, it has been impossible heretofore, to assess bactericidal concentrations of antibiotics by this method.

It is an object of this invention to provide a simple method for assessing the antibacterial activity of antibiotics.

It is another object of this invention to provide a simple method for assessing the bactericidal activites of antibiotics on agar plates.

Yet another object of the invention is to provide a method for determining both the bacteriostatic and bactericidal activities of β-lactam antibiotics on agar plates.

Still another object of the invention is to provide a device for facilitating the carrying out of such method and more particularly to provide a device for uniformly applying an antibiotic inactivating enzyme onto the agar plates.

These and other objects and advantages of the invention will become apparent from a consideration of the following description of the invention.

The method of the invention comprises preparing a plurality of agar plates with serial two-fold dilution of antibiotic concentration, inoculating test bacteria into the agar plates, determining bacteriostatic activity by the conventional method on the basis of the presence or absence of the formation of macroscopic bacterial colonies after incubation of the inoculated plates for a fixed period of time and under predetermined laboratory conditions, thereafter uniformly dispersing an antibiotic inactivating enzyme onto the agar surface for inactivating the antibiotic and so as to obtain an antibiotic concentration on the agar surface of almost zero, and assessing bactericidal activity by the presence or absence of formation of any new macroscopic bacterial colonies after incubation of the agar plates for a fixed period of time and under specified conditions.

The invention also provides an apparatus particularly adapted for uniformly distributing, i.e spraying the antibiotic inactivating enzyme onto the agar plate comprising a base having affixed to the upper surface thereof both a petri dish holding stand and a strut, an arm lever mounted for sliding upward and downward movement on the strut, and for having its length decreased or increased with respect to the strut and attached to the free end of the arm lever a vessel having means associated therewith for bringing about the discharge of the liquid contained in the vessel in the form of a finely atomized spray in the direction of the petri dish holding stand.

Figure 2:
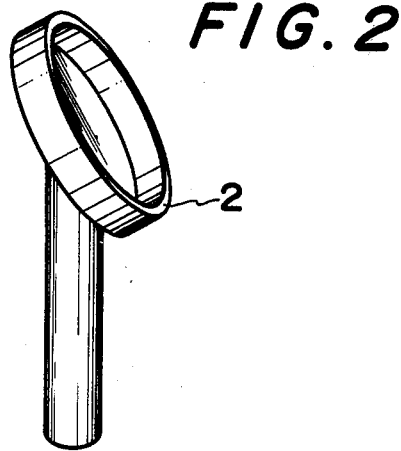

The device of the invention is further illustrated in the accompanying drawing, in which FIG. 1 is a perspective view of the enzyme dispersing device of the invention; and FIG. 2 is an elevation of the petri dish holding stand portion of the device shown in FIG. 1.

As already noted, the invention relates to a method for assessing the antibacterial activity of antibiotics and namely their bacteriostatic and bactericidal activities. As used herein, bacteriostatic activity means that antibiotic activity sufficient only to inhibit the growth of the bacteria and bactericidal activity means that antibiotic activity sufficient to kill the bacteria. These activities are defined as the antibiotic concentrations which inhibit or kill the test bacteria (MIC and MBC respectively).

In accordance with the invention the MIC and MBC in agar was determined by the steps of preparing a plurality of agar plates with serial two-fold dilutions of each antibiotic. The test bacteria was inoculated on the agar plates. These inoculated plates were incubated at 37° C. overnight. The MIC was defined as the minimal antibiotic concentration that yielded complete inhibition of the bacteria on the plates. The enzyme solution (for inactivating the antibiotic) was then sprayed uniformly onto the plates using an atomizer. The plates were incubated again at 37° C. overnight. The minimal antibiotic concentration at which no visible growth occurred on the plates after incubation was defined as the MBC.

Preferably the enzyme solution is sprayed onto the plates using the enzyme distributing device of the invention which comprises a base 1 having arranged on the upper surface thereof a petri dish holding stand 2 (inclined with respect to the base) and a strut 3. An arm lever 4 is mounted on bar 9 affixed to collar 10 provided on strut 3 for sliding upward and downward movement thereon. Arm lever 4 is also provided with a plate 8 for adjusting its length with respect to the strut 3. Attached to the free end of lever 4 is a vessel 7 having compressible means 5, pipe 6a and atomizing head 6b associated therewith for discharging liquid contained in the vessel in the form of a finely atomized spray. As can be appreciated from the drawing, the petri dish is held or supported in the stand 2. The arm lever 4 is fixed by means not shown, for instance a screw, at a proper position on the strut 3.

In the method of the present invention different bacterial strains such as *Staphylococcus aureus,* enterococcus, Escherichia coli and *Klebsiella pneumoniae* can be inoculated onto the surface of the agar plates prepared for example on the basis of heart infusion agar (Difco) and containing various concentrations of antibiotics, for instance benzylpenicillin, ampicillin, amoxicillin, cephalexin, cephaloridine, cephalothin and cefazolin. A phosphate buffer solution (pH adjusted to 7.2) is advantageously used for the dilution of both the antibiotic and specimen. The inoculated plates are incubated at 37° C. for a fixed time, preferably about 24 hours. Depending on the concentration of the antibiotic, bacterial growth results and is clearly visible on the plates. Generally, in the plates having the high concentration of antibiotic, the antibiotic inhibits the bacterial growth while on the plates having low antibiotic concentrations distinctly visible and typical growth is observed. The lowest antibiotic concentration which serves to inhibit the growth of the bacteria on the plates is defined as the minimal inhibitory concentration (MIC).

As antibiotic inactivating enzyme, a $\beta$-lactamase can be used in the second step of applicant's method. Thus a commercial preparation of penicillinase (Penase, Difco; 50,000 U/ml) can be used to inactivate the penicillins. One milliliter of this enzyme solution inactivates up to 5,000,000 $\mu$g of each benzylpenicillin, ampicillin and amoxicillin in liquid medium.

The antibiotic inactivating enzyme is uniformly sprayed onto the surface of the agar plate, for instance using the apparatus of the invention. The enzyme sprayed agar plates are then placed in an incubator and maintained therein at 37° C. for about 24 hours. The bacterial cells which have survived on the plates begin to grow again forming typical visible growth patterns. Thus the fact that the plates may have evidenced no visible growth at the time just prior to the enzyme application does not mean that there were no surviving cells present. Rather the non-visible, but entirely viable cells which had been inhibited by the presence of the antibiotic now have the opportunity to grow by virtue of the inactivation of the antibiotic.

The minimal antibiotic concentration which completely inhibited bacterial growth as evaluated by the naked eye after the second incubation is designated as the minimal bactericidal concentration (MBC) of the antibiotic.

The following example is given in order to more completely illustrate the invention but is in no wise to be construed as limitative of the scope thereof.

EXAMPLE

Determination of MIC and MBC in Agar

Heart infusion agar plates (10 ml) with serial two-fold dilutions of each $\beta$-lactam antibiotic were prepared in 90 mm petri dishes. Inoculum sizes were undiluted ($10^8$ to $10^9$ cells/ml), and overnight cultures were diluted to a $10^{-2}$ dilution ($10^6$ to $10^7$ cells/ml) and a $10^{-4}$ dilution ($10^4$ to $10^5$ cells/ml). Each of these inocula was inoculated on the agar plates by the use of inocula-replicating apparatus and transferred by a 0.001 ml calibrated loop. These Plates were incubated at 37° C. overnight. The MIC was defined as the minimal antibiotic concentration that yielded complete inhibition of the bacteria on the plates. $\beta$-Lactamase solution was then sprayed uniformly onto the plates by using a perfume atomizer. The amount of the enzyme solution added was about 0.1 ml per plate. These plates were incubated again at 37° C. overnight. The minimal antibiotic concentration at which no visible growth occurred on the plates after incubation was arbitrarily defined as MBC. MIC and MBC values were studied in relation to inocumul size.

Confirmative Study of Antibiotic Inactivation on the Agar Plates

A control study was also carried out simultaneously using the same agar plates that were being used for the determination of MBC values. The strain most susceptible to the antibiotic, the MIC of which was being determined by the study, was selected as the control organism. A loopful (0.001 ml) of a $10^{-4}$ culture (the greatest dilution used in the study) of the control strain was additionally inoculated on the agar plates that had already undergone $\beta$-lactamase treatment. After further incubation at 37° C. overnight, the plates showing visible growth of the control bacteria were considered to be optimal for determining MBC values.

In the above example, the antibiotic inactivating enzyme was delivered onto the agar plate using the apparatus of the invention. Specifically the inactivating enzyme solution was introduced into vessel 7. A petri dish was placed in petri dish fixing stand 2. As pipe 6a is constructed of a flexible material, the distributing device 6b can be positioned with respect to the petri dish so that when the compressible means 5 is repeatedly squeezed, the enzyme solution will be delivered in the form of an atomized spray onto the surface of the petri dish. The length of arm lever 4 can also be adjusted as required with respect to the distance of the distributing device 6b from the petri dish thereby permitting variations in the qualitative distribution of the enzyme solution onto the surface of the petri dish.

In accordance with a further embodiment of the invention, the petri dish holding stand 2 can be mounted for varying the angle of the petri dish with respect to the base 1, for instance so that the petri dish is maintained at an angle of 45° with respect to the base. This has the advantage that if an excess of enzyme inactivating solution is delivered onto the surface of the petri dish it does not accumulate as large droplets on the agar plate surface and bring about mixing of adjacent inoculated bacterial cells on the agar plate.

In the operation of the device, the volume of the enzyme solution is maintained at a constant level and the device more or less calibrated to deliver a constant amount of solution.

The present invention permits the assaying of the antibacterial activity of a broad range of antibiotics with respect to a large varied number of bacteria. It further permits the determination of the bactericidal activity of such antibiotics in a simple and time-saving manner.

Since it is possible to assess the antibacterial activity of various antibiotics, bacteriostatic and also bactericidal, against strains simultaneously in a simple, economic and rapid manner, the invention permits the comparison of the antibacterial activity of various antibiotics with respect to given strains in a most simple and time-saving manner.

We claim:

1. Method for assessing antibacterial activity of antibiotics on agar plates, comprising the steps of preparing a plurality of agar plates each containing a different concentration of the antibiotic, the concentration being varied by means of a series of twofold dilutions of the antibiotic; incubating the plates for a predetermined period of time; determining the minimal antibiotic concentration (MIC) yielding complete inhibition of growth of the bacteria on the plate; uniformly spraying an antibiotic inactivating enzyme onto the agar plates for inactivating the antibiotic; incubating the sprayed plates for a predetermined period of time; and again determining the minimal antibiotic concentration (MBC) at which no visible bacterial growth occurs on the plates after the second incubation.

2. Method according to claim 1, wherein said incubation in each instance occurs overnight.

3. Method according to claim 1, wherein said incubation in each instance is for 24 hours.

4. Method according to claim 1, wherein said antibiotic inactivating enzyme is $\beta$-lactamase.

5. Method according to claim 1, wherein said antibiotic inactivating enzyme is added in an amount of 0.1 ml per plate.

6. Method according to claim 1, wherein said antibiotic is a member selected from the group consisting of $\beta$-lactamase unstable penicillins and cephalosporins.

7. Method according to claim 1, wherein said bacteria are selected from the group consisting of *Staphylococcus aureus*, enterococcus, Escherichia coli and *Klebsiella pneumoniae*.

8. Apparatus for uniformly distributing inactivating enzyme onto an agar plate comprising a base having affixed to the upper surface thereof a petri dish holding stand and strut, an arm lever mounted for sliding upward and downward movement on said strut, the lever being capable of having its length increased or decreased with respect to said strut, a vessel for holding liquid inactivating enzyme attached to the free end of said arm lever, and means associated with said vessel for bringing about the discharge of liquid contained in said vessel in the form of a finely atomized spray in the direction of said petri dish holding stand.

9. Apparatus according to claim 8, wherein said petri dish holding stand is mounted for varying the angle of the petri dish with respect to said base.

10. Apparatus according to claim 8, wherein said means associated with said vessel include a tubular conduit connecting said vessel with a distributing device and compressible means for forcing said fluid out of said vessel into said tubular conduit for delivery out of said distributing device.

* * * * *